United States Patent [19]
Greenwald

[11] Patent Number: 5,521,191
[45] Date of Patent: May 28, 1996

[54] METHOD FOR TREATMENT OF ARTERIAL STENOSIS

[75] Inventor: James E. Greenwald, St. Louis, Mo.

[73] Assignee: Washington University, St. Louis, Mo.

[21] Appl. No.: 324,816

[22] Filed: Oct. 17, 1994

[51] Int. Cl.$^6$ .................................................. A61K 31/52
[52] U.S. Cl. ............................................................ 514/262
[58] Field of Search ............................................. 514/262

[56] References Cited

U.S. PATENT DOCUMENTS 4,496,544  1/1985  Needleman ................................ 514/13

OTHER PUBLICATIONS

Dundore, et al., Eur. J. Pharmacol. 249, 293–297 (1993).
McMahon, et al., J. Pharmacol. Exp. Therap. 251, 1000–1005 (1989).
Buchholz, et al., Fed. Am. Soc. Exp. Biol. J3, A1186 (1989).
Lugnier, et al., Am. J. Physiol. 262, H654–H660 (1992).
Burns, Chem. Absts. 117: 22314 (1992).
Wilkins et al. J. Clin. Invest. 85, 1274–1279 (1990).

*Primary Examiner*—Jerome D. Goldberg
*Attorney, Agent, or Firm*—Scott J. Meyer

[57] ABSTRACT

A method is disclosed for treatment of arterial stenosis which comprises administering to a warm-blooded mammal following balloon angioplasty a small but effective amount of zaprinast sufficient to inhibit intimal hyperplasia in said mammal.

2 Claims, 4 Drawing Sheets

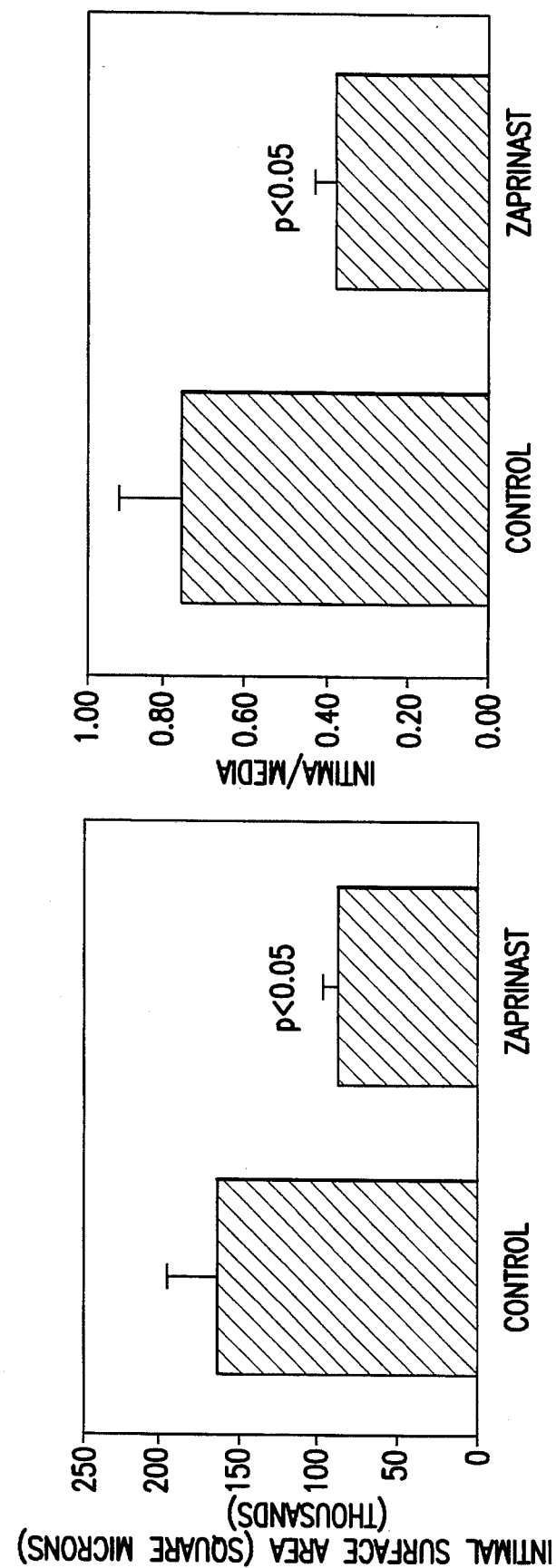

METHOD FOR TREATMENT OF ARTERIAL STENOSIS

BACKGROUND OF THE INVENTION

The present invention relates to a method for the treatment of arterial stenosis and, more particularly, to a method of inhibiting intimal hyperplasia following balloon angioplasty by treatment with zaprinast.
(NOTE: Literature references on the following background information and on the conventional test methods and laboratory procedures well known to the person skilled in the art and other such state-of-the-art techniques as used herein are indicated in parentheses and appended at the end of the specification.)

Balloon angioplasty is a widely used medical procedure with an initial success rate of greater than ninety percent (26). Success is defined as a reduction of the original stenosis by more than fifty percent. However, arterial restenosis is a significant complication and occurs in approximately 17–40% of all patients (1–5). Mechanisms contributing to vascular restenosis include platelet aggregation (27), local vasoconstriction (28), and intimal proliferation of smooth muscle cells. Treatment with anticoagulants (29), smooth muscle vasodilators (30), and antiproliferative agents (31) have not successfully inhibited clinical restenosis. Recently, it has been suggested that activation of the vascular renin angiotensin system (RAS) in diseased vessels stimulates intimal smooth muscle hyperplasia (32). Human trials evaluating angiotensin converting enzyme inhibitors for arterial restenosis have not been successful (33), but further trials are ongoing.

Intimal hyperplasia has been described in part as an uncontrolled growth response of vascular smooth muscle cells (VSMCs) following vascular reconstructions (e.g. balloon angioplasty and bypass grafting) and is a leading cause of surgical reintervention for restenosis (1–5). Although there is no available therapy to prevent the formation of intimal hyperplasia, recent advancements were made by McNamara and colleagues (6). They demonstrated that the intimal proliferative response was inhibited by altering the level of the naturally occurring metabolite nitric oxide (NO) with L-arginine administration in animal models of balloon angioplasty. Their hypothesis was that NO, formed by the vascular endothelium, would inhibit intimal hyperplasia similar to its ability to inhibit VSMC proliferation in vitro (7–9). In addition, Furuya and colleagues (10) recently showed that administering C-type natriuretic peptide (CNP) also attenuated intimal thickening after vascular injury in rats.

CNP is a member of the natriuretic family of peptides which also includes atrial natriuretic peptide (ANP) and brain natriuretic peptide (BNP). CNP is synthesized in the vascular endothelial cell (11,12), and its receptor, guanylyl cyclase type B (GC-B), is expressed in the vascular smooth muscle cell (13,14). Quiescent smooth muscle cells express minimal amounts of GC-B; however, during growth and replication GC-B expression is dramatically increased both in vitro (13,14) and in vivo (10). CNP, like NO, increases intracellular cGMP upon receptor activation, and potently inhibits cellular proliferation and DNA synthesis in cultured rat VSMCs (15,16). However, since some of the biologies of NO and the natriuretic peptides have been attributed to non-cGMP mediated mechanisms (17), the present inventor sought to evaluate the role of cellular CGMP in the proliferative and growth response of VSMCs. One means to increase cellular CGMP levels is to inhibit its degradation to its 5'-monophosphate. Cyclic-AMP and cGMP are metabolized by cellular phosphodiesterase enzymes. Currently, five specific classes of enzymes have been defined. The type five enzyme is a cGMP specific phosphodiesterase designated as PDE-V.

BRIEF DESCRIPTION OF THE INVENTION

In accordance with the present invention, a method is provided for inhibiting intimal hyperplasia. The method comprises parenterally administering to a warm-blooded mammal following balloon angioplasty a small but effective amount of zaprinast. Zaprinast is the generic name of 1,4-dihydro-5-[2-propoxyphenyl]-7H-1,2,3-triazolo[4,5-d]pyrimidine-7-one, which is also known chemically as 2-o-propoxyphenyl-8-azapurin-6-one (M&B 22948).

Zaprinast is a known selective inhibitor of the cyclic-GMP-specific PDE (PDE-V) (18). It elevates cellular cGMP, and has been shown to potentiate the pharmacologic profile of both NO (19) and the natriuretic peptides (20).

As illustrated herein, zaprinast has been found to inhibit vascular smooth muscle cell (VSMC) proliferation in vitro and the intimal proliferative response induced by balloon angioplasty of rat carotid artery.

In cell culture, zaprinast (1 mM) inhibited serum-induced VSMC proliferation by 80%. In rat model of balloon angioplasty, continuous intravenous administration of zaprinast (25 mg/kg/day for 14 days, begun one day prior to arterial injury) inhibited the intimal lesion size by 51%. Zaprinast infusion had no effect on mean arterial pressure, while plasma cGMP levels were elevated eight-fold. Urinary cGMP and sodium excretion was also significantly elevated with zaprinast treatment. Hence, inhibition of vascular cGMP metabolism with zaprinast is an efficacious treatment of restenosis secondary to balloon angioplasty.

A significant advantage of zaprinast is that it is a small organic molecule that is readily absorbed (25). Based on the results shown herein, it is deemed to be useful in the inpatient or outpatient management of atherosclerosis and arterial restenosis.

It will be appreciated that although the method of the invention is illustrated in particular hereinbelow with the rat species, it is also useful for other warm-blooded mammals, e.g., humans, in an analogous manner.

DETAILED DESCRIPTION OF THE INVENTION

While the specification concludes with claims particularly pointing out and distinctly claiming the subject matter regarded as forming the present invention, it is believed that the invention will be better understood from the following preferred embodiments of the invention taken in conjunction with the accompanying drawings.

BRIEF DESCRIPTION OF THE DRAWINGS

FIGS. 2A and 2B show the effect of zaprinast on intimal hyperplasia in the rat. Rat carotid arteries were injured by balloon angioplasty on day one, then harvested for histology fourteen days later. Zaprinast infusion 25 mg/kg/day was begun one day prior to injury and continued until animal sacrifice. FIG. 2A shows intimal hyperplasia expressed as a function of intimal surface area, and FIG. 2B shows intimal hyperplasia expressed as a function of the ratio of the intima to media surface area. Values are expressed as the mean±standard error of the mean of eight animals. Statistical significance was compared versus vehicle infusion.

Figure 1:
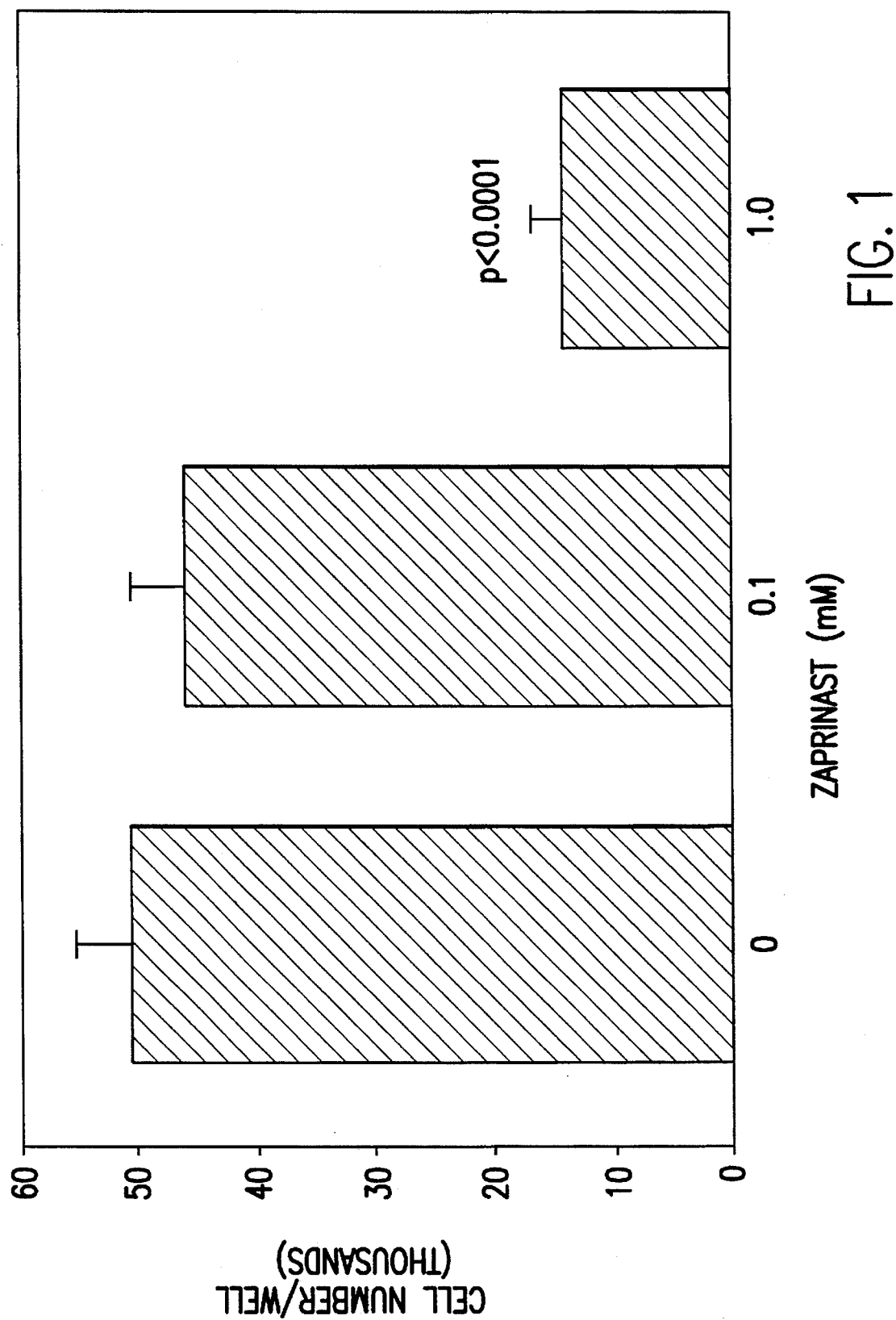
FIG. 1 shows the effect of zaprinast on rat aortic smooth muscle cell proliferation in culture. Cells were seeded at a density of 10,000 cells/well and incubated in the absence or presence of drug for three days. Values are expressed as the mean±standard error of the mean of four individual determinations. Statistical significance was compared versus the no drug group.
Figure 3A:
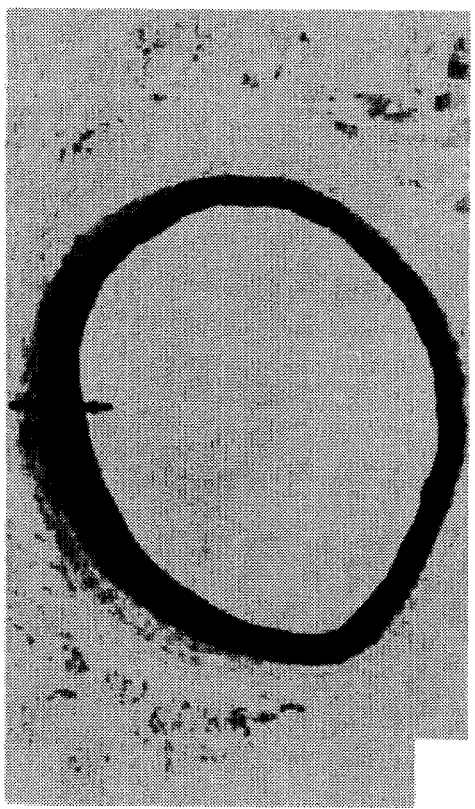
FIGS. 3A, 3B, 3C and 3D show representative histologic cross-sections of rat carotid artery after balloon angioplasty, (A) zaprinast-treated, 25× magnification; (B) zaprinast-treated, 10× magnification; (C) vehicle-treated, 25× magnification; (D) vehicle-treated, 10× magnification. a=vessel media, b=vessel intima.
Figure 3B:
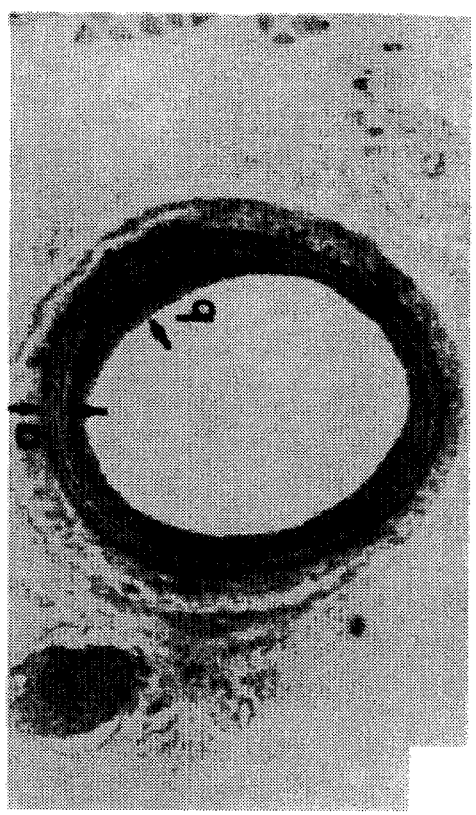
Figure 3C:
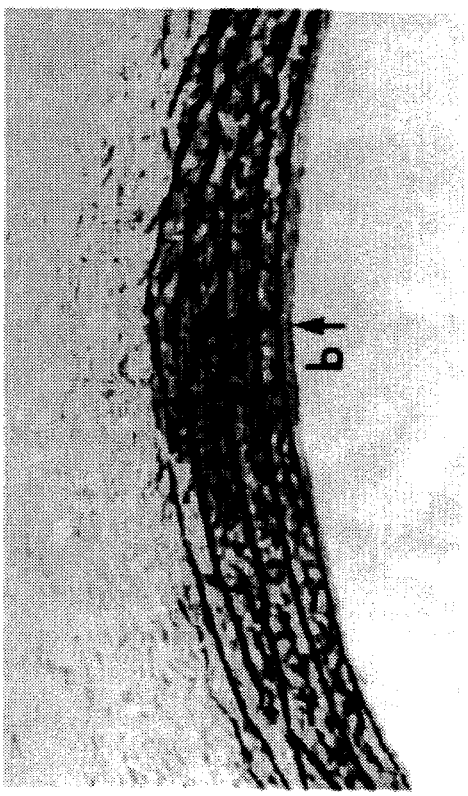
Figure 3D:
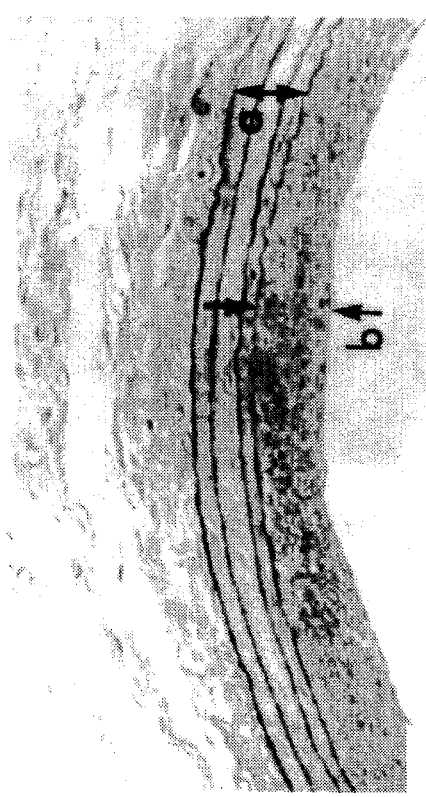

In order to illustrate the invention in greater detail, the following specific laboratory examples were carried out. Although specific examples and details are illustrated herein, it will be appreciated that the invention is not limited to these specific examples or their details.

EXAMPLES

Materials and Methods

Cell Culture. Rat carotid VSMCs were isolated by conventional explant culture as previously described (21,22). VSMCs were grown in Dulbecco's Modified Eagle Medium (DMEM; Gibco BRL, Grand Island, N.Y.) supplemented with 10% fetal bovine serum (FBS; HyClone Labs Inc., Logan, Fla.), 100 units/ml penicillin, and 100 µg/ml streptomycin and were passed 1:2 at confluence. To determine if the cultured cells were SMCs and not endothelial cells or fibroblasts, immunohistochemical staining was performed with antibodies to SMC specific α-actin and Factor VIII (Sigma Chemical Company, St. Louis, Mo.). For all tests, cells were used at passage 10 to 15.

Cell Proliferation Assay. To determine the effect of zaprinast on SMC proliferation, cells were seeded at 10,000 cells per well on 6-well plates, and the cells were kept in growth-arrest medium for three days. Growth arrest medium consisted of 0.1% FBS-DMEM. The medium was then changed to 10% FBS-DMEM, and various doses of zaprinast were added. The cells were permitted to grow for three days in the presence of zaprinast. At the end of this time, the cells were removed from the plates by trypsinization, and counted with a Coulter counter (Model AM; Coulter Electronics, Hialeah, Fla.). Each experiment was done in quadruplicate and repeated at least two times.

Balloon Angioplasty and Drug Infusion. The procedure employed herein for carotid arterial injury is well known in the literature (21,22). Briefly, male Sprague-Dawley rats (weight 400–450 grams) were anesthetized with an intramuscular dose of ketamine (40 mg/kg), acepromazine (1 mg/kg), and xylazine (20 mg/kg) and aseptically prepped. An Alzet minipump (Alzet Corp., Palo Alto, Calif.) filled with either normal saline or zaprinast (50 mg/ml), was implanted subcutaneously in the animals' back and the infusion tubing was inserted into the femoral vein. On the following day, the animals were reanesthetized and a 3 French embolectomy catheter was inserted in the left external carotid artery through a midline incision to the neck. Endothelial denudation and medial injury were performed by filling the balloon with 0.1 ml of saline and pulling it antegrade along the entire length of the artery three times to assure uniform injury. On day 14 post injury, the animals were reanesthetized as described above. Left carotid arteries were harvested, perfusion fixed with 4% paraformaldehyde at physiologic pressures and processed for histology. Animal care complied with the "Principles of Laboratory Animal Care" and the "Guide for the Care and Use of Laboratory Animal" (NIH Publication No. 80-23, revised 1985).

Histology. The perfusion-fixed arteries were embedded in paraffin and sectioned (2 µm) every 5 mm. The sections were stained with Verhoeff van Giesem. Video images of the light microscopic slides (Zeiss microscope) were projected on a television monitor, total intimal and medial area determined by computer-aided planimetry (Microsystems, Boyce Scientific, St. Louis, Mo.), and the intima: media area ratio determined.

Physiological parameters. On day zero prior to Alzet pump implantation and day 14 post angioplasty, arterial blood pressure was measured in anesthetized animals with a Harvard blood pressure monitor (model VT-15C). All animals were placed in metabolic cages one day prior to sacrifice (day 14) for 24-hour urine collections in order to quantitate urinary sodium and cGMP excretion. While in the metabolic cages, animals were not fed but allowed free access to tap water. During days one to thirteen, rats were fed standard rat chow (Purina) and allowed free access to tap water. Urinary and plasma cGMP was measured using a commercial enzyme immunometric assay (EIA) (Caymen Chem., Ann Arbor, Mich.). Urine volume was measured gravimetrically, and urine sodium was determined by flame photometry (Instrumentation Laboratory, model 943).

Reagents. Zaprinast was kindly provided by the Monsanto Corporation (St. Louis, Mo.).

Statistics. Statistics were performed using the statistical analysis software package (Instat, GraphPad, San Diego. Calif.). All data were expressed as mean±standard error of the mean (SEM). Statistical analysis was performed by two-way analysis of variance and student's t-test was used to evaluate the significance of difference. A probability of less than 0.05 was considered statistically significant.

Results

It has been previously demonstrated that agents which stimulate the production of cGMP such as ANF (23), CNP (13), and NO donors (24) are able to inhibit proliferation of smooth muscle cells in culture. Therefore, the initial tests were designed to evaluate whether the inhibition of PDE-V by zaprinast, thus increasing endogenous cellular levels of cGMP, would inhibit smooth muscle cell proliferation. Rat aortic smooth muscle cells were seeded at a density of 10,000 cells/well. In the presence of 10% FBS, cell number increased five-fold in three days (FIG. 1). In the presence of growth arrest media, no cellular proliferation was noted. One millimolar zaprinast inhibited FBS-induced smooth muscle cell proliferation by approximately 80%, while one tenth this dose demonstrated little to no inhibition. Theoretically, it is possible that zaprinast treatment decreased the number of cells by causing cellular toxicity or death. This was not the case since all zaprinast-treated cells effectively excluded trypan blue. Furthermore, daily monitoring of the cell culture media demonstrated no floating or dead cells. These data demonstrate that cellular cGMP is an endogenous inhibitor of VSMC hyperplasia.

Balloon angioplasty of an artery produces intimal thickening and many times results in a significant stenosis. The intimal thickening is secondary to migration of smooth muscle cells from the media into the intima, and subsequent intimal smooth muscle cell proliferation. Since it was demonstrated that zaprinast inhibits smooth muscle cell proliferation in vitro, it was next evaluated whether zaprinast would also inhibit intimal hyperplasia in the injured rat carotid artery. Zaprinast was administered as a continuous intravenous infusion (25 mg/kg/day) beginning one day prior to angioplasty and continuing until the time of animal sacrifice. As depicted in FIG. 2A, zaprinast significantly inhibited intimal hyperplasia by 45%. Similarly, when intimal hyperplasia was expressed as the ratio of the surface area of the intima to the surface area of the media (microns$^2$), zaprinast inhibited restenosis by 51% (FIG. 2B). Representative histological cross-sections of carotid artery from rats treated with either zaprinast or vehicle are shown in FIG. 3. These data demonstrate that inhibition of PDE-V with zaprinast is an effective modality to inhibit angioplasty-induced intimal hyperplasia in the rat.

Figure 4:
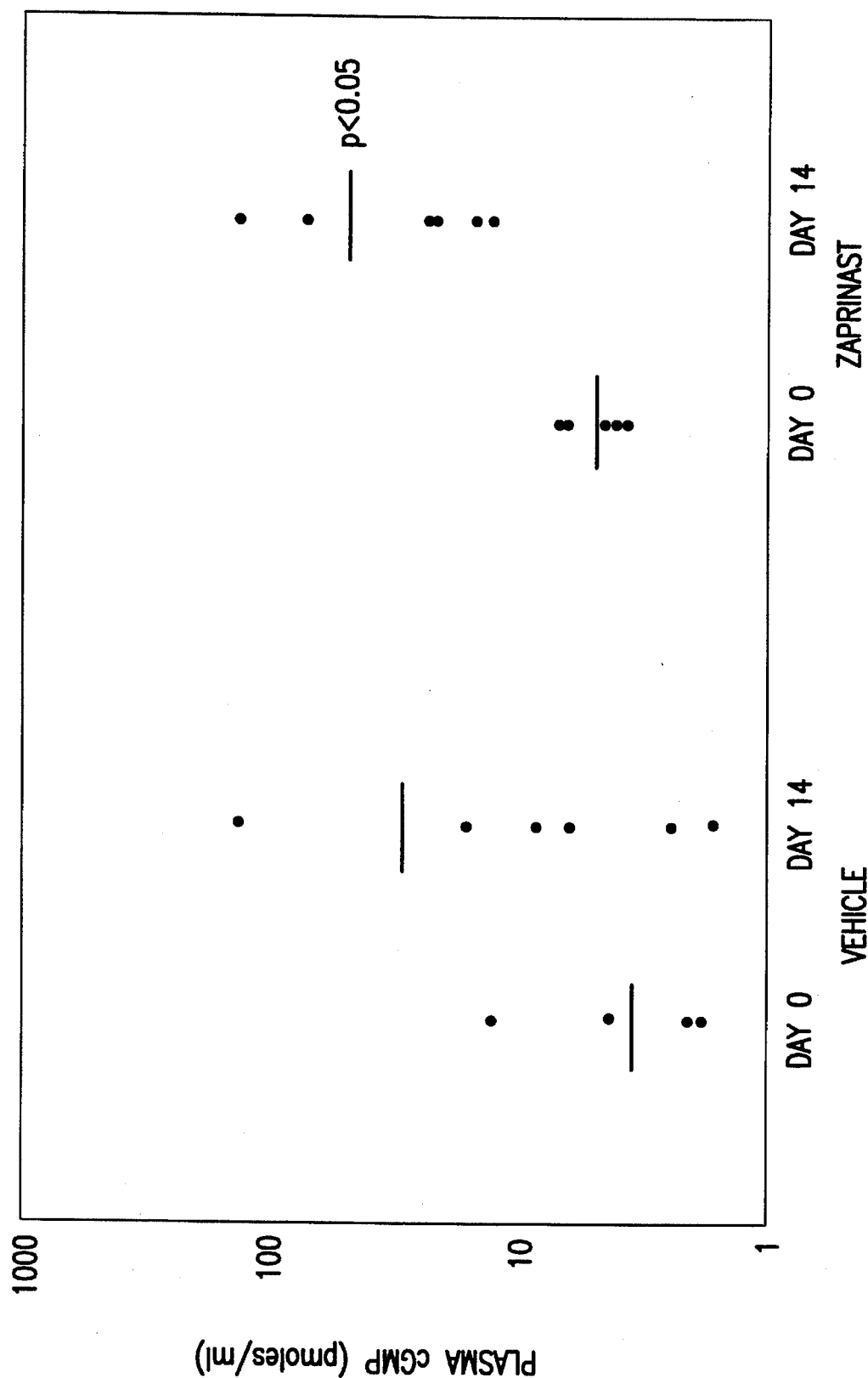
FIG. 4 shows plasma cGMP concentrations in vehicle and zaprinast-treated rats. Plasma cGMP was measured in animals prior to and fourteen days after beginning vehicle or zaprinast infusions. Values are expressed as the mean±standard error of the mean of six rats. Statistical significance was compared between day zero and day fourteen within each treatment group.

The pharmacologic profile of zaprinast in rats includes vasorelaxation and sodium excretion (25), but at much higher doses (200 mg/kg/day) than were administered herein. When administered at 25 mg/kg/day), zaprinast had no effect on mean arterial blood pressure (FIG. 4). However, plasma cGMP levels were significantly elevated approximately eight-fold fourteen days after zaprinast treatment (FIG. 5). Therefore, these data confirm the continuous delivery of zaprinast to the rat for the full fourteen days of the test protocol.

Similar to ANF, zaprinast stimulates urinary sodium and cGMP excretion (25). Consistent with these findings, urinary sodium excretion was increased two-fold in the zaprinast treatment group. This natriuresis was accompanied by a similar increase in urinary cGMP excretion (Table 1).

TABLE 1

| Treatment | $U_{Na}V$ (meg/day) mean ± SEM | $U_{cGMP}V$ (pmoles/min) mean ± SEM |
|---|---|---|
| Control | 0.9 ± 0.1 | 33.0 ± 5.5 |
| Zaprinast | 2.1 ± 0.4** | 62.5 ± 10.3** |

**$p < 0.05$

TABLE 1 shows the urinary sodium and cGMP excretion in vehicle and zaprinast-treated rats. Animals were placed into individual metabolic cages 24 hours prior to sacrifice for urine collection.

The administration of the zaprinast to a host or patient subjected to balloon angioplasty can be carried out by conventional means, preferably in formulations with pharmaceutically acceptable diluents and carriers. The amount to be administered must be an effective amount, that is, an amount which is medically beneficial but does not present toxic effects which overweigh the advantages which accompany its use.

It is expected that the adult human dose would range upward from about 100 mg of the active drug in a daily dose less than about 100 mg/Kg of body weight, and preferably in a daily dose of from about 1.5 to about 25 mg/Kg of body weight. A suitable route of administration is orally in the form of capsules, tablets, syrups, elixirs and the like, although parenteral administration can also be used such as, e.g., intravenous administration in admixture with physiologic saline and/or suitable buffers. Appropriate formulations of the active drug in pharmaceutically acceptable diluents and carriers in therapeutic dosage form can be prepared by reference to general texts in the field well known to the person skilled in the art such as, e.g., *Remington's Pharmaceutical Sciences*, Ed. Arthur Osol, 16th ed. 1980, Mack Publishing Co., Easton, Pa., and 18th ed. 1990.

Various other examples will be apparent to the person skilled in the art after reading the present disclosure without departing from the spirit and scope of the invention. It is intended that all such other examples be included within the scope of the appended claims.

REFERENCES

1. McBride, W., Lange, R. A., & Hillis L. D. (1988) N. Engl. J. Med. 318, 1734–1737.
2. Liu, M. W., Roubin, G. S., & King, S. B. Jr. (1989) Circulation 79, 1374–1387.
3. Nobuyoshi, M., Kimura, T., Nosaka, H., et al. (1988) J. Am. Coll. Cardiol. 12, 616–623.
4. Serruys, P. W., Luijten, H. E., Beatt, K. J., et at. (1988) Circulation 77, 361–371.
5. Callow, A. D. (1982) Surg. Clin. North Amer. 62, 501–513.
6. McNamara, D. B., Bedi, B., Aurora, H., Tena, L., Ignarro, L. J., Kadowitz, P. J., & Akers, D. L. (1993) Biochem. Biophys. Res. Commun. 193, 291–296.
7. Ignarro, L. J., Buga, O. M., Wood, K. S., Byrns, R. E., & Chaudhuri, G. (1987) Proc. Natl. Acad. Sci. USA 84, 9265–9269.
8. Palmer, R. M. J., Ferrige, A. G., & Moncada, S. (1987) Nature 327, 524–526.
9. Garg, U. C., & Hassid, A. (1989) J. Clin. Invest. 83, 1774–1777.
10. Furuya, M., Aisaka, K., Miyazaki, T., Honbou, N., Kawashima, K., Ohno, T., Tanaka, S., Minamino, N., Kangawa, K., & Matsuo, H. (1993) Biochem. Biophys. Res. Commun. 193, 248–253.
11. Stingo, A. J., Clayell, A. L., Heublein, D. M., Wei, C., Dittelkow, M. R., & Burnett, J. C. Jr. (1992) Am. J. Physiol. 263, H1318–HI321.
12. Suga, S., Itoh, H., Komatsu, Y., Ogawa Y., Yoshimasa, T., & Nakao,K. (1993) Endocrinology 133, 3038–3041.
13. Porter, J. G., Catalano, R., McEnroe, G., Lewicki, J. A., & Porter, A. A. (1992) Am J. Physiol. 263, C1001–C1006.
14. Fujio, N., Gossard, F., Bayard, F., & Tremblay, I. (1994) Hypertnesion 23, 908–913.
15. Furuya, M., Takehisa, M., Minamitake, Y., Kitajima, Y., Hayashi, Y., Ohnuma, N., Ishihara, T., Minamino, N., Kangawa, K., & Matsuo, H. (1990) Biochem. Biophys. Res. Commun. 170, 201–210.
16. Furuya, M., Yoshida, M., Hayashi, Y., Ohnuma, N., Minamino, N., Kangawa, K., & Matsuo, H. (1990) Biochem. Biophys. Res; Commun. 177, 927–931.
17. Levin, E. R. (1993) Am. J. Physiol. 264, E483–E489.
18. Beavo, J. A., & Reifsnyder, D. H. (1990) Trends in Pharmacological Sciences 11, 150–155. 19. Dundore, R. L., Pratt, P. F., Hellenbeck, W. D., Wassey, M. L., Silver, P. J., & Buchholz, R. A. (1990) European Pharmacol. 185, 91–97.
20. Wilkins, W. R., Settle, S. L., & Needleman, P. (1990) J. Clin. Invest 85, 1274–1279.

21. Choi, E. T., Sehgal, N., Sun, S., Trachtenberg, J. D., Ryan, U. S., & Callow, A. D. (1994) in Modem Vascular Surgery, ed. Chang, J. B. (Springer-Verlag, New York, N.Y.), Vol. 6, pp. 2840.
22. Choi, E. T., Engel, L., Callow, A. D., Sun, S., Trachtenberg, J. D., Santoro, S. A., & Ryan, U. S. (1994) 3. Vasc. Surg. 19, 125–134.
23. Abell, T. J., Richards, A. M., Ikram, H., Espiner, E. A., & Yandle, T. (1989) Biochem. Biophys. Res. Commun. 160, 1392–1396.
24. Garg, U. C., & Hassid, A. (1989) J. Clin. Invest. 83, 1774–1777.
25. McMahon, E. G., Palomo, M. A., Mehta, P., & Oilins, G. M. (1989) J. Pharmacol. Exp. Therap. 251, 1988–1005.
26. Grossman, W., & Baim, D. S. (1991) in Principles of Internal Medicine, eds. Wilson, J. D., Braunwald, E., Isselbacher, K. J., Petersdorf, R. G., Martin, J. B., Fauci, A. S., & Root, R. K. (McGraw-Hill, New York, N.Y.), Vol. 12, pp. 877479.
27. Fingerle, J., Johnson, R., Clowes, A. W., Majesky, M. W., & Reidy, M. A. (1989) Proc. Natl. Acad. Sci. USA 86, 8412–8416.
28. Fuster, V., Badimon, L., Badimon, J. J., & Chesebro, J. H. (1992) New Engl. J. Med. 326, 242–318.
29. Lam, J. Y. T., Chesebro, J. H., & Steele, P. M. (1991) 84, 814–820.
30. Jackson, C. L., Bush, R. C., & Bowyer, D. E. (1988) Atherosclerosis 69, 115–122.
31. Muller, D. W., Ellis, S. G., & Topol, E. J. (1991) J. Am. Coll. Cardiol. 17(6 Suppl B), 126B–131B.
32. Rakugi, H., Jacob, J. H., Ingelfinger, J. R., Krieger, J. E., Dzau, V. J., & Pratt, R. E. (1990) Hypertension 16, 3435–352.
33. Faxon, D. P. (1992) Circulation 86, 100–110.

What is claimed is:

1. A method for inhibiting intimal hyperplasia comprising administering to a warm-blooded mammal following balloon angioplasty a small but inhibitorily effective amount of zaprinast.

2. The method of claim 1 in which the amount of zaprinast administered is from about 1.5 to about 25 mg/Kg per day.

* * * * *